United States Patent [19]
Lin et al.

[11] Patent Number: 5,654,247
[45] Date of Patent: Aug. 5, 1997

[54] METHOD FOR THE REACTIVATION OF A DEACTIVATED HYDROCARBON ISOMERIZATION CATALYST

[75] Inventors: Fan-Nan Lin, Bartlesville, Okla.; Daniel T. Fernald; Floyd H. Holland, both of Borger, Tex.

[73] Assignee: Phillips Petroleum Company, Bartlesville, Okla.

[21] Appl. No.: 442,932

[22] Filed: May 17, 1995

Related U.S. Application Data

[63] Continuation-in-part of Ser. No. 207,988, Mar. 8, 1994, abandoned.

[51] Int. Cl.$^6$ .............................. B01J 20/34; B01J 38/10; C07C 5/23
[52] U.S. Cl. .............................. 502/53; 585/670; 585/748
[58] Field of Search .............................. 502/53; 585/670, 585/748

[56] References Cited

U.S. PATENT DOCUMENTS

| | | | |
|---|---|---|---|
| 1,447,689 | 3/1923 | Richardson | 502/53 |
| 2,418,023 | 3/1947 | Frey | 502/53 |
| 3,352,941 | 11/1967 | Schuen et al. | 502/53 |
| 3,389,191 | 6/1968 | Estes | 502/53 |
| 3,449,264 | 6/1969 | Myers . | |
| 3,764,633 | 10/1973 | Garnet et al. | 585/670 |
| 4,039,604 | 8/1977 | Myers et al. . | |
| 4,404,118 | 9/1983 | Herskovitsl | 502/53 |
| 5,039,639 | 8/1991 | Khare | 502/36 |

*Primary Examiner*—Glenn A. Caldarola
*Assistant Examiner*—Elizabeth D. Wood
*Attorney, Agent, or Firm*—Charles W. Stewart

[57] ABSTRACT

Described is a novel method by which the activity of a deactivated or partially deactivated paraffin isomerization catalyst is enhanced or reactivated. The isomerization catalyst undergoes a deactivation period followed by a reactivation period during which isomerizable hydrocarbons are simultaneously isomerized during the catalyst reactivation.

8 Claims, No Drawings

METHOD FOR THE REACTIVATION OF A DEACTIVATED HYDROCARBON ISOMERIZATION CATALYST

This application is a continuation-in-part of prior application Ser. No. 08/207,988, filed Mar. 8 1994, and now abandoned.

This invention relates to an isomerization process and the reactivation of deactivated isomerization catalyst.

Isomerization of normal paraffins is widely used in refinery processes for the upgrading of lower valued hydrocarbons to hydrocarbons of higher value. In recent years there has been an increased interest in the isomerization of normal paraffins having 4–7 carbon atoms to isoparaffins, particularly the isomerization of normal butane to isobutane. Due to recent federal mandates concerning the vapor pressure of gasoline, high vapor pressure components, such as normal butane, are sought to be removed from the gasoline pool. But, upon the removal of such high vapor pressure components there must be some other use for such components. This makes butane isomerization beneficial; since, it isomerizes n-butane to isobutane, which can be used as a feedstock for various other refinery processes, such as alkylation and etherification, that produce high octane gasoline components.

A problem that is encountered in the isomerization of normal butane under process conditions of low molar feed ratios of hydrogen to butane is the rapid deactivation of the isomerization catalyst. This deactivation is reflected in a decline of the isomerization catalyst activity, as represented by the reactor temperature required for a given conversion, over a time period of use of the catalyst. There are believed to be a number of causes of the catalyst deactivation which include the accumulation of carbon or coke and, in the case of butane isomerization, the accumulation of $C_5$ to $C_8$ hydrocarbons on the isomerization catalyst surface which tend to have a poisoning effect on the catalyst.

One practice used to reactivate an isomerization catalyst once it has lost a portion of its original activity is to discontinue the isomerization reaction by removing feed and proceeding with a reactivation procedure for restoring the catalyst activity. This method of reactivation has the disadvantage of necessarily requiring the periodic discontinuation of the isomerization reaction thereby resulting in lost production or through-put. Another practice is to offset the activity decline by raising reactor temperature. This procedure has the disadvantage of accelerating the rate at which the catalyst deactivates by increasing the production of coke.

It is thus an object of this invention to provide a method by which the activity of a deactivated or partially deactivated isomerization catalyst can be reactivated or enhanced.

Another object of this invention is to provide a method by which the activity of an isomerization catalyst can be enhanced during the simultaneous use of the catalyst in the isomerization of hydrocarbons.

Still, another object of this invention is to provide a method which permits the economical isomerization of normal paraffin hydrocarbons to isoparaffins where there is utilized a low molar ratio of hydrogen-to-hydrocarbon feed while achieving an exceptionally long useful operating life for the associated isomerization catalyst.

Thus, the invention is a method for the reactivation or partial reactivation of a partially deactivated isomerization catalyst. This reactivation method includes contacting for a time period a feed mixture containing hydrocarbons and hydrogen with an isomerization catalyst. The feed mixture has a comparatively low molar ratio of hydrogen-to-hydrocarbon in the range of from about 0.05:1 to about 0.25:1 and is contacted with the isomerization catalyst at a temperature in the range of from about 200° F. to about 350° F. After such contacting time period the molar ratio of hydrogen-to-hydrocarbon of said feed mixture is substantially increased for an additional reactivation time period. Thereafter, the molar ratio of hydrogen-to-hydrocarbon of said feed mixture is reduced to the same molar ratio range utilized in the contacting step.

Other objects and advantages of the invention will be apparent from the detailed description of the invention and the appended claims.

The feed mixture to be charged to an isomerization reaction zone, which can be defined by a reactor vessel, and contacted with an isomerization catalyst contained therein will comprise hydrocarbons and hydrogen. The isomerizable hydrocarbons to which the process of this invention is applicable include normal paraffins containing four or more carbon atoms per molecule including n-butane, n-pentane, n-hexane, n-heptane and the like. Preferred hydrocarbons are those containing 4 to 7 carbon atoms and, most preferred, is normal butane.

The isomerization catalyst utilized in the process of this invention can be any suitable catalyst which contains platinum, chlorine and alumina. Alkane isomerization catalysts which catalyze the conversion of $C_4$ to $C_7$ alkanes (preferably n-butane) to isoalkanes are well known. They can be prepared by processes described in the patent literature, such as, for example, U.S. Pat. Nos. 3,449,264 and 4,014,948. Preferred alkane isomerization catalysts are also commercially available, e.g., from UOP, Inc., Des Plaines, Ill., and from the Catalyst and Chemicals Division of Engelhard Corporation, Newark, N.J. Generally, these catalysts contain about 0.01–10 (preferably about 0.1–1) weight percent Pt and about 1–10 (preferably about 2–6) weight percent Cl.

Chloride promoter and hydrogen are introduced into the hydrocarbon feed to form a feed mixture to be contacted with the isomerization catalyst contained in the isomerization zone. The organic chloride promoters, for example, $CCl_4$, $C_2Cl_4$ and $C_4H_9Cl$, are introduced in the amounts of 50 to 200 ppm by weight chlorine per hydrocarbon feed. The concentration of the hydrogen in the feed mixture during the contacting step shall be maintained at at least about 0.05:1 moles of hydrogen per mole of hydrocarbon feed but not exceeding about 0.25:1 moles of hydrogen per mole of hydrocarbon feed. The preferred molar ratio of hydrogen to hydrocarbon feed in the feed mixture contacted with the isomerization catalyst is in the range of from about 0.1:1 to about 0.225:1 and, most preferred, the molar ratio can be in the range of from 0.15:1 to 0.225:1.

The average contacting temperature within the isomerization zone during the contacting step of the process shall be no greater than about 350° F. with the contacting temperature preferably being in the range of from about 200° F. to about 350° F. Most preferably, the contact temperature can be in the range of from 250° F. to 340° F. It is not desirable to operate the contacting step above about 350° F. under conditions when the molar ratio of hydrogen-to-hydrocarbon feed in the feed mixture charged to the isomerization reactor is lower than about 0.25:1 due to the high rate of catalyst deactivation that occurs as a consequence of such extraordinary process conditions. One advantage of the inventive process described herein, however, is that the hydrogen-to-hydrocarbon feed ratio of the isomerization feed mixture is significantly lower than that which the prior art has taught to be acceptable or preferred.

The present invention provides a method which uniquely permits the isomerization of isomerizable hydrocarbons in an isomerization zone and in the presence of an inordinately low concentration of hydrogen under severe temperature conditions followed by a subsequent increase in the molar ratio of hydrogen-to-hydrocarbon feed in order to restore at least a portion of the activity of the isomerization catalyst that is lost as a result of such unusual contact conditions. What is particularly unusual about the instant invention is that, to restore the activity of the catalyst after having been contacted with a feed mixture containing hydrocarbons and a comparatively low concentration of hydrogen for a period of time sufficient to reduce the activity of the isomerization catalyst, the molar ratio of hydrogen-to-hydrocarbon feed can be increased for a sufficient period of time such that the activity of the isomerization catalyst is enhanced or restored or reactivated. The higher molar ratio of hydrogen-to-hydrocarbon can be maintained during the reactivation period while simultaneously isomerizing the isomerizable hydrocarbons in the feed mixture.

In another embodiment of the invention, the process temperature can also be raised during the catalyst reactivation step concurrently with the increase in the molar ratio of hydrogen-to-hydrocarbon feed. While an improvement or an enhancement of the partially deactivated isomerization catalyst is achieved through increasing of the molar ratio of hydrogen-to-hydrocarbon feed above that of the contacting or deactivating step, a significantly greater improvement in the catalyst activity can be achieved through the concurrent increase in the process temperature during the reactivation step.

The process temperature of the reactivation step can be maintained for a period of time of at least about 370° F. Preferably, the reactivation temperature is maintained in the range of from about 375° F. to about 450° F. and, most preferably, it can be in the range of from 380° F. to 425° F.

During the reactivation step, the molar ratio of hydrogen-to-hydrocarbon feed of the feed mixture to the isomerization zone is increased subsequent to the deactivation or contacting step, preferably along with an increase in the temperature, to at least about 0.3:1. Preferably, the molar ratio of hydrogen-to-hydrocarbon feed of the feed mixture can be at least about 0.4:1 and, most preferably it can be at least 0.55:1.

It is desirable to maintain the molar ratio of hydrogen-to-hydrocarbon feed during the reactivation step such that there is simultaneous isomerization of the isomerizable hydrocarbons in the hydrocarbon feed. Generally, to achieve catalyst reactivation while simultaneously isomerizing the isomerizable hydrocarbon in the hydrocarbon feed, the molar ratio of hydrogen-to-hydrocarbon feed should be no more than about 30:1, but, preferably, no more than about 25:1. Most preferably, the upper limit for the hydrogen-to-hydrocarbon feed ratio during the reactivation step can be 22:1. Thus, the desirable range for the molar ratio of hydrogen-to-hydrocarbon feed during the reactivation step can be from about 0.3:1 to about 30:1, preferably from about 0.4:1 to about 25:1 and, most preferably, from 0.55:1 to 22:1.

Once the temperature and the feed mixture ratio of hydrogen-to-hydrocarbon feed are increased after the deactivation time period, they are maintained within the desirable ranges for a reactivation time period sufficient to enhance the activity of the partially deactivated isomerization catalyst.

The reactivation time period is influenced by a number of factors, but the most appropriate determinant of the amount of time required for reactivating the partially deactivated isomerization catalyst is the volume of paraffins contacted with the catalyst during the deactivation step as defined by the ratio of volumetric charge of paraffin, based on standard conditions of 60° F. and 1 atmosphere, to the isomerization zone to the mass weight of the isomerization zone catalyst with such ratio of volumetric charge-to-catalyst having units of cubic feet per pound ($ft^3/lb$). Generally, for a fixed quantity of catalyst contained in an isomerization zone, the ratio of volumetric charge of hydrocarbon to the isomerization zone during the contacting or deactivation step to the volumetric charge of hydrocarbon to the isomerization zone during the reactivation step, hereinafter referred to as deactivation charge to activation charge ratio, can be at least about 4.0:1. Preferably, the ratio can be about 5.0:1 and, most preferably, the ratio is at least 7.5:1.

If during the reactivation step only the hydrogen-to-hydrocarbon feed molar ratio is increased as opposed to increasing both the temperature and hydrogen-to-hydrocarbon feed ratio, a longer reactivation time period will be required to achieve a desired enhancement in catalyst activity. Thus, the volumetric ratio of deactivation charge to activation charge can be at least about 5.0:1, preferably at least about 7.5:1 and, most preferably, at least 10.0:1.

After the reactivation time period has concluded and sufficient activity of the catalyst has been restored, the process conditions of the isomerization zone are returned to those conditions utilized for the contacting or deactivation step. That is, the process temperature can be in the range of no greater than about 350° F., preferably, in the range of from about 200° F. to about 350° F. and, most preferably, in the range of from 250° F. to 340° F. The hydrogen-to-hydrocarbon feed ratio of the feed mixture charged to the isomerization zone shall also be lowered to no greater than about 0.25:1, preferably, to the range from about 0.1:1 to about 0.225:1 and, most preferably, from 0.15:1 to 0.225:1.

The following examples are presented to further illustrate the invention and are not to be considered as limiting the scope of the invention.

EXAMPLE I

This example illustrates the unexpected performance of the invention which permits the reactivation of a deactivated catalyst while simultaneously utilizing the catalyst in the isomerization of paraffin hydrocarbons in the presence of 80 ppm by weight chlorine per butane feed. The data presented demonstrate that an isomerization catalyst can undergo a period wherein it is contacted with isomerizable hydrocarbons for a deactivation period, under deactivation conditions; and, thereafter, the isomerization catalyst is contacted with the same isomerizable hydrocarbons, but under reactivation conditions, for a reactivation period whereby a portion of the lost activity during the deactivation period is restored. This novel process has the benefit of prolonging the useful life of the isomerization catalyst over the life of such catalyst when the cyclic activation and reactivation steps of the inventive process are not used.

The data presented in Table I was developed by testing the novel reactivation procedure in a Phillips Petroleum Company butane isomerization plant located at Borger, Tex. A butane feed was charged to the isomerization reactor along with added hydrogen so as to provide the desired hydrogen-to-hydrocarbon reactor feed ratio. The conversion rate, defined as a product ratio of the mole fraction of isobutane in the product to the total mole fraction of n-butane and isobutane in the product, was maintained substantially constant at about 0.55 by adjusting reactor inlet temperature.

Thus, the reactor inlet temperature provided the measure of catalyst deactivation with any increase in reactor inlet temperature required to maintain conversion being an indicator of catalyst deactivation. As the data clearly demonstrate, for the deactivation period during which the molar ratio of hydrogen-to-hydrocarbon in the reactor feed was below 0.3:1 the isomerization catalyst gradually lost activity. However, during the first reactivation period in which both reactor temperature and hydrogen-to-hydrocarbon molar ratio were simultaneously increased, a portion of the activity lost during the deactivation stage is restored as evidenced by the lower reactor inlet temperature required to maintain a fixed conversion rate.

In the subsequent reactivation periods, the temperature was not significantly increased, but the molar ratio of hydrogen-to-hydrocarbon was increased. This increase in molar ratio of hydrogen-to-hydrocarbon also resulted in a restoration of a portion of the activity that was lost in the preceding deactivation step.

For comparison, data is present in Table II for butane isomerization without the periodic use of a reactivation step as is used in the novel process. The data in Table II show a useful life for the catalyst of 32 time periods as opposed to the significantly greater useful life of the catalyst used in the novel process of greater than 45 time periods. The data show that the useful life of the isomerization catalyst can be extended by the cyclic reactivation of the novel process.

TABLE I

Experimental Data for Butane Isomerization With Reactivation

| Time Periods On-Stream | Reactor Inlet Temp.**, °F. | $H_2$/HC | I-$C_4$ In Product % |
|---|---|---|---|
| Deactivation Period | | | |
| 0 | 270 | 0.167 | 56.1 |
| 1 | 283 | 0.160 | 61.1 |
| 2 | 250 | 0.095 | 62.1 |
| 3 | 260 | 0.286 | 51.9 |
| 4 | 260 | 0.280 | 51.9 |
| 5 | 258 | 0.294 | 51.2 |
| 6 | 279 | 0.244 | 59.6 |
| 7 | 280 | 0.252 | 59.5 |
| 8 | 284 | 0.244 | 61.0 |
| 9 | 279 | 0.238 | 59.2 |
| 10 | 295 | 0.216 | 60.7 |
| 11 | 282 | 0.202 | 58.9 |
| 12 | 289 | 0.059 | 60.1 |
| 13 | 299 | 0.172 | 54.8 |
| 14 | 290 | 0.195 | 59.7 |
| Reactivation Period | | | |
| 15* | 338 | 0.595 | 60.2 |
| Deactivation Period | | | |
| 16 | 310 | 0.195 | 61.2 |
| 17 | 304 | 0.166 | 59.2 |
| 18 | 296 | 0.178 | 58.6 |
| 19 | 302 | 0.164 | 58.5 |
| 20 | 304 | 0.163 | 58.1 |
| 21 | 308 | 0.164 | 57.0 |
| 22 | 302 | 0.165 | 59.3 |
| 23 | 312 | 0.168 | 59.5 |
| 24 | 301 | 0.242 | 58.7 |
| 25 | 299 | 0.252 | 59.3 |
| 26 | 305 | 0.287 | 56.9 |

TABLE I-continued

Experimental Data for Butane Isomerization With Reactivation

| Time Periods On-Stream | Reactor Inlet Temp.**, °F. | $H_2$/HC | I-$C_4$ In Product % |
|---|---|---|---|
| Reactivation Period | | | |
| 27* | 313 | 0.490 | 56.3 |
| 28* | 309 | 0.526 | 56.7 |
| Deactivation Period | | | |
| 29 | 301 | 0.296 | 57.0 |
| 30 | 300 | 0.266 | 56.0 |
| 31 | 300 | 0.287 | 58.0 |
| 32 | 296 | 0.166 | 57.4 |
| 33 | 287 | 0.283 | 57.5 |
| 34 | 285 | 0.287 | 57.5 |
| 35 | 292 | 0.267 | 57.5 |
| 36 | 291 | 0.273 | 57.5 |
| 37 | 292 | 0.271 | 57.4 |
| 38 | 302 | 0.163 | 55.7 |
| 39 | 292 | 0.294 | 53.7 |
| Reactivation Period | | | |
| 40* | 292 | 0.533 | 41.9 |
| 41* | 290 | 0.522 | 41.6 |
| Deactivation Period | | | |
| 42 | 290 | 0.272 | 39.3 |
| 43 | 293 | 0.281 | 39.4 |
| 44 | 293 | 0.290 | 56.1 |
| 45 | 291 | 0.293 | 56.1 |

*Reactivation Periods Using Enhanced $H_2$/HC Streams.
**Note that the Catalyst Bed Temperature Can be Approximately 50° F. Higher Due to the Exothermic Isomerization Reaction

TABLE II

Experimental Data for Butane Isomerization Without Reactivation

| Time Period On-Stream | Reactor Inlet Temp**, °F. | $H_2$/HC | I-$C_4$ In Product Mole % |
|---|---|---|---|
| 1 | 302 | 0.386 | 59.0 |
| 4 | 302 | 0.376 | 57.8 |
| 5 | 305 | 0.242 | 59.6 |
| 6 | 305 | 0.239 | 58.8 |
| 7 | 310 | 0.227 | 59.8 |
| 10 | 319 | 0.230 | 58.9 |
| 16 | 335 | 0.231 | 60.2 |
| 18 | 345 | 0.225 | 58.3 |
| 23 | 340 | 0.215 | 57.0 |
| 27 | 349 | 0.219 | 47.1 |
| 28 | 358 | 0.215 | 56.3 |
| 30 | 333 | 0.056 | 57.6 |
| 31 | 344 | 0.235 | 50.2 |
| 32 | 360 | 0.239 | 50.6 |

**Note that the catalyst bed temperature can be approximately 50° F. higher due to the exothermic isomerization reaction.

EXAMPLE II

This example illustrates that there can be an upper limit for the hydrogen-to-hydrocarbon mole ratio used for the reactivation step of the inventive method during which simultaneous reactivation and isomerization occur. The inventive method includes a reactivation step in which the mole ratio of hydrogen-to-hydrocarbon is increased above such ratio used during the deactivation step with simultaneous isomerization.

For this Example II, a laboratory scale butane isomerization experiment in the presence of 200 ppm by weight chlorine per butane feed was conducted using a standard, commercially available isomerization catalyst. The data collected from conducting this isomerization experiment are Presented in Table III below.

TABLE III

Catalyst Reactivation of Butane Isomerization Catalyst

| Catalyst Age (hours) | $H_2$:HC Molar Ratio | IC4 In Product (%) | Comment |
|---|---|---|---|
| 82 | 0.17 | 33.7 | prior to reactivation |
| 99 | 16.6 | 22.2 | one hours reactivation |
| 107 | 0.21 | 45.6 | after reactivation |

The catalyst age presented in Table III is in hours of run time, but the presented catalyst age should approximate the on-stream time periods presented in Table I of Example I after making adjustments for the amounts of catalyst and the volume of feed contacted with such catalyst. The time periods indicated in Table I of Example I are all substantially equal periods of time.

The reactor temperature was maintained substantially constant during the butane isomerization experiment, thus, the butane conversion varied with deactivation and reactivation. As can be seen from the data of Table III, a one hour reactivation of a deactivated catalyst was conducted by raising the hydrogen-to-hydrocarbon ratio to 16.6. The conversion declined from 33.7 percent to 22.2 percent during the reactivation period. There was still conversion of the hydrocarbon during the reactivation period, thus, simultaneous isomerization was occurring during the reactivation step. After the one hour reactivation, the hydrogen-to-hydrocarbon ratio was reduced to 0.21:1. The activity of the catalyst was observed to be improved after the reactivation period with the conversion increasing to 45.6 percent. This demonstrates that a hydrogen-to-hydrocarbon ratio of about 17:1 can suitably reactivate a deactivated catalyst while simultaneously isomerizing hydrocarbons.

EXAMPLE III

This Example III provides further experimental data to support the upper limit for the hydrogen-to-hydrocarbon mole ratio used for the reactivation step of the inventive method during which simultaneous reactivation and isomerization occur. This experiment was conducted in substantially the same manner as the experiment of Example II.

TABLE IV

Experimental Data for Butane Isomerization with Reactivation

| Catalyst Age (hours) | $H_2$:HC Molar Ratio | IC4 in Product (%) |
|---|---|---|
| Deactivation | | |
| 99 | 0.12 | 55.1 |
| 111 | 0.12 | 53.0 |
| Reactivation | | |
| 121 | 43.2 | 12 |
| Deactivation | | |
| 121.5 | 0.12 | 53.1 |
| 122 | 0.12 | 47.4 |

TABLE IV-continued

Experimental Data for Butane Isomerization with Reactivation

| Catalyst Age (hours) | $H_2$:HC Molar Ratio | IC4 in Product (%) |
|---|---|---|
| Reactivation | | |
| 125 | 6.5 | 22.4 |
| Deactivation | | |
| 126 | 0.12 | 52.9 |
| 127 | 0.12 | 53.8 |
| Reactivation | | |
| 128 | 22.4 | 13.0 |
| Deactivation | | |
| 128.5 | 0.12 | 50.6 |
| 129 | 0.12 | 54.9 |
| 141 | 0.12 | 55.9 |

The data presented in Table IV show that the reactivation of a partially deactivated isomerization catalyst is not achievable with a hydrogen to hydrocarbon feed molar ratio of about 43:1. As can be seen from the data, a return to the deactivation step after a period of reactivation with a feed having a $H_2$/HC molar ratio of 43:1 showed little improvement in catalyst activity as evidenced by the insignificant change in percent conversion to isobutane. The reactivation step using a feed having a $H_2$/HC molar ratio of 22.4:1 showed a significant improvement in the catalyst activity. These data indicate that the upper limit for the $H_2$/HC molar ratio for achieving reactivation of a partially deactivated isomerization catalyst while simultaneously isomerizing isomerizable hydrocarbons is between about 20:1 to about 40:1. Thus, a probable upper limit for the feed $H_2$/HC molar ratio during the reactivation step of the inventive method is about 30:1. However, the preferred ratio for the upper limit is about 25:1 and, most preferred, it is about 22:1.

While this invention has been described in detail for the purpose of illustration, reasonable variations and modifications are possible by those skilled in the art. Such variations and modifications are within the scope of the described invention and the appended claims.

That which is claimed is:

1. A method for the reactivation of a partially deactivated isomerization catalyst, said method comprising the steps of:
   contacting a hydrocarbon feed with an isomerization catalyst contained in a reaction zone in the presence of hydrogen and at a mole ratio of said hydrogen-to-said hydrocarbon feed in the range of from about 0.05:1 to about 0.25:1 and at a temperature in the range of from about 200° F. to about 350° F. for a deactivation time period such that the activity of said isomerization catalyst is reduced to provide said partially deactivated isomerization catalyst;
   after said deactivation time period, increasing said mole ratio of hydrogen-to-said hydrocarbon feed to at least about 0.3:1 but no more than about 17:1 for a reactivation time period such that the activity of said partially deactivated isomerization catalyst is enhanced; and
   thereafter, returning said mole ratio of hydrogen-to-said hydrocarbon feed to the range of from about 0.05:1 to about 0.25:1 and said temperature to the range of from about 200° F. to about 350° F.

2. A method as described in claim 1 wherein the reaction zone temperature is increased during said reactivation time period to at least about 370° F.

3. A method as described in claim 2, wherein the ratio of the volume of hydrocarbon feed contacted with said isomerization catalyst during said deactivation time period to the volume of hydrocarbon feed contacted with said isomerization catalyst during said reactivation time period is at least about 4:1.

4. A method as described in claim 3 wherein said hydrocarbon feed comprises a paraffin selected from the group consisting of butane, pentane, hexane and heptane.

5. A method as described in claim 4 wherein said hydrocarbon feed comprises normal butane.

6. A method as described in claim 1 wherein the ratio of the volume of hydrocarbon feed contacted with said isomerization catalyst during said deactivation time period to the volume of hydrocarbon feed contacted with said isomerization catalyst during said reactivation time period is at least about 4:1.

7. A method as described in claim 6 wherein said hydrocarbon feed comprises a paraffin selected from the group consisting of butane, pentane, hexane and heptane.

8. A method as described in claim 7 wherein said hydrocarbon feed comprises normal butane.

* * * * *